US008231526B2

(12) United States Patent
Yabe et al.

(10) Patent No.: US 8,231,526 B2
(45) Date of Patent: Jul. 31, 2012

(54) MEDICAL APPARATUS (75) Inventors: Yusuke Yabe, Hachioji (JP); Shinji Yamashita, Tachikawa (JP); Yoshimine Kobayashi, Hachioji (JP); Koji Omori, Hachioji (JP); Masato Toda, Hachioji (JP); Takeshi Suga, Hino (JP); Kazuma Kaneko, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1050 days.

(21) Appl. No.: 12/173,064

(22) Filed: Jul. 15, 2008

(65) Prior Publication Data

US 2009/0036743 A1 Feb. 5, 2009

(30) Foreign Application Priority Data

Jul. 31, 2007 (JP) ................................ 2007-199743

(51) Int. Cl.
*A61B 1/06* (2006.01)
(52) U.S. Cl. ....................................... 600/160; 600/177
(58) Field of Classification Search .................. 600/103, 600/118, 160, 180, 181; 348/68; 362/574
See application file for complete search history.

(56) References Cited

U.S. PATENT DOCUMENTS

| 7,062,311 | B1 * | 6/2006 | Sendai et al. ................. 600/407 |
| 7,179,222 | B2 * | 2/2007 | Imaizumi et al. ............. 600/109 |
| 7,226,412 | B2 * | 6/2007 | Ueno et al. .................... 600/178 |
| 7,258,663 | B2 * | 8/2007 | Doguchi et al. .............. 600/109 |
| 7,470,229 | B2 * | 12/2008 | Ogawa et al. ................. 600/180 |
| 7,658,710 | B2 * | 2/2010 | Ueno et al. .................... 600/160 |
| 7,670,286 | B2 * | 3/2010 | Imaizumi et al. ............. 600/160 |
| 7,762,950 | B2 * | 7/2010 | Hirata ........................... 600/179 |
| 7,907,169 | B2 * | 3/2011 | Sugimoto ....................... 348/65 |
| 2003/0120129 | A1 | 6/2003 | Nakamura |

FOREIGN PATENT DOCUMENTS

| EP | 1 488 732 A1 | 12/2004 |
| EP | 1 839 558 A1 | 10/2007 |
| JP | 06-245899 A | 9/1994 |
| JP | 06-261326 A | 9/1994 |
| JP | 08-254659 A | 10/1996 |
| JP | 2000-261714 A | 9/2000 |

(Continued)

OTHER PUBLICATIONS

Extended European Search Report dated Aug. 24, 2010.

*Primary Examiner* — Philip R Smith
(74) *Attorney, Agent, or Firm* — Scully, Scott, Murphy & Presser, P.C.

(57) ABSTRACT

A medical apparatus includes: a first illumination window through which a first illumination light from a first light source is irradiated to a subject; a second illumination window at different position than the first illumination window, through which a second illumination light from a second light source is irradiated to the subject; an electronic image pickup section which picks up subject images; an image creation section which generates observation images based on image pickup signals obtained by the electronic image pickup section; a light adjustment section which synchronously adjusts respective amounts of illumination lights irradiated from the first and second illumination windows; and a control unit which controls the light adjustment section or image creation section to maintain color tone of the observation image to a predetermined one according to increase/decrease of the illumination light amount from the first illumination window.

12 Claims, 8 Drawing Sheets

FOREIGN PATENT DOCUMENTS

| | | |
|---|---|---|
| JP | 2002-165756 A | 6/2002 |
| JP | 2002-336196 | 11/2002 |
| JP | 2003-079570 A | 3/2003 |
| JP | 2007-143647 A | 6/2007 |
| WO | WO 2006/077799 A1 | 7/2006 |
| WO | WO 2007/072633 A1 | 6/2007 |

\* cited by examiner

MEDICAL APPARATUS

This application claims benefit of Japanese Application No. 2007-199743 filed on Jul. 31, 2007 the contents of which are incorporated by this reference.

BACKGROUND OF THE INVENTION

1. Field of the Invention

The present invention relates to a medical apparatus that allows normal observation by white light as well as observation of a fluorescent image.

2. Description of Related Art

In recent years, endoscopes have come to be widely used in the medical and industrial application fields. In the medical application field, there have been realized normal endoscope apparatuses for obtaining a normal image by white light, as well as endoscope apparatuses for obtaining a fluorescent image.

For such an endoscope apparatus for obtaining a fluorescent image, a technique is disclosed that enables picking up both normal and fluorescent images with one image pickup device, as described in, e.g., Japanese Unexamined Patent Publication No. 2002-336196. This publication also discloses a configuration in which the endoscope apparatus includes two image pickup devices for separately photographing normal and fluorescent images.

SUMMARY OF THE INVENTION

A medical apparatus according to the present invention includes: a first illumination window through which a first illumination light from a first light source is irradiated to a subject; a second illumination window provided at a position different from that of the first illumination window, through which a second illumination light from a second light source is irradiated to the subject; an electronic image pickup section which picks up an image of the subject; an image creation section which generates an observation image based on an image pickup signal obtained by the electronic image pickup section; a light adjustment section which synchronously adjusts respective amounts of illumination lights irradiated from the first illumination window and the second illumination window; and a control unit which controls the light adjustment section or the image creation section such that a color tone of the observation image is maintained to a predetermined color tone according to increase/decrease of the amount of the illumination light from the first illumination window.

The above and other objects, features and advantages of the invention will become more clearly understood from the following description referring to the accompanying drawings.

BRIEF DESCRIPTION OF THE DRAWINGS

FIG. 11 relates to the third embodiment of the present invention and is a view showing electronic shutter values (CCD exposure times) of the autofluorescence, the G reflection light, and the R reflection light when the light emitting diode is turned on.

DETAILED DESCRIPTION OF PREFERRED EMBODIMENTS

Embodiments of the present invention are described below referring to the drawings. Note that in the following descriptions, the embodiments of the present invention use an endoscope apparatus as a medical apparatus to be inserted in a body cavity to observe biological tissues.

First Embodiment

First, a first embodiment is described.

Figure 1:
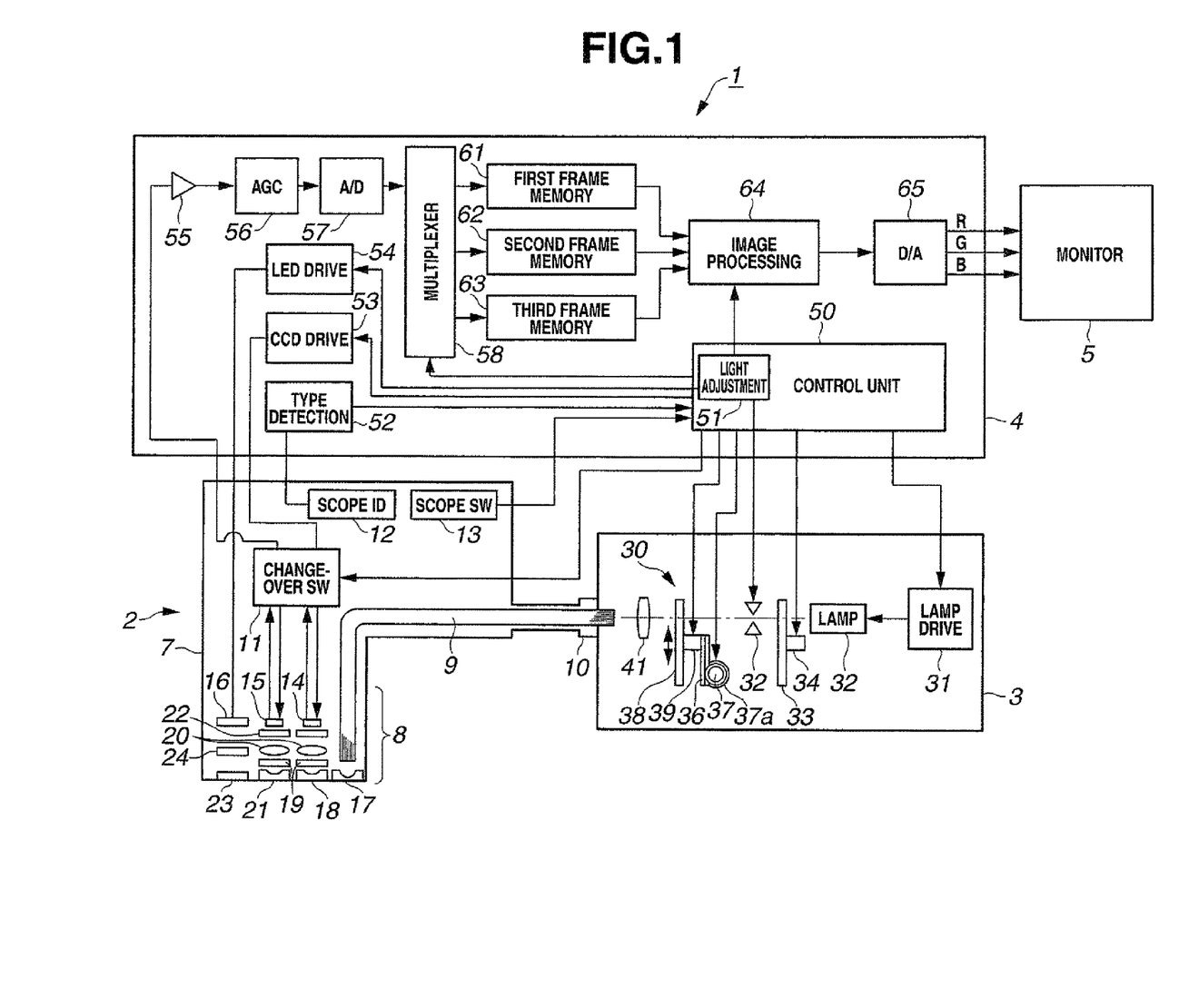
FIG. 1 relates to a first embodiment of the present invention and is a block diagram showing the entire configuration of an endoscope apparatus.
Figure 2:
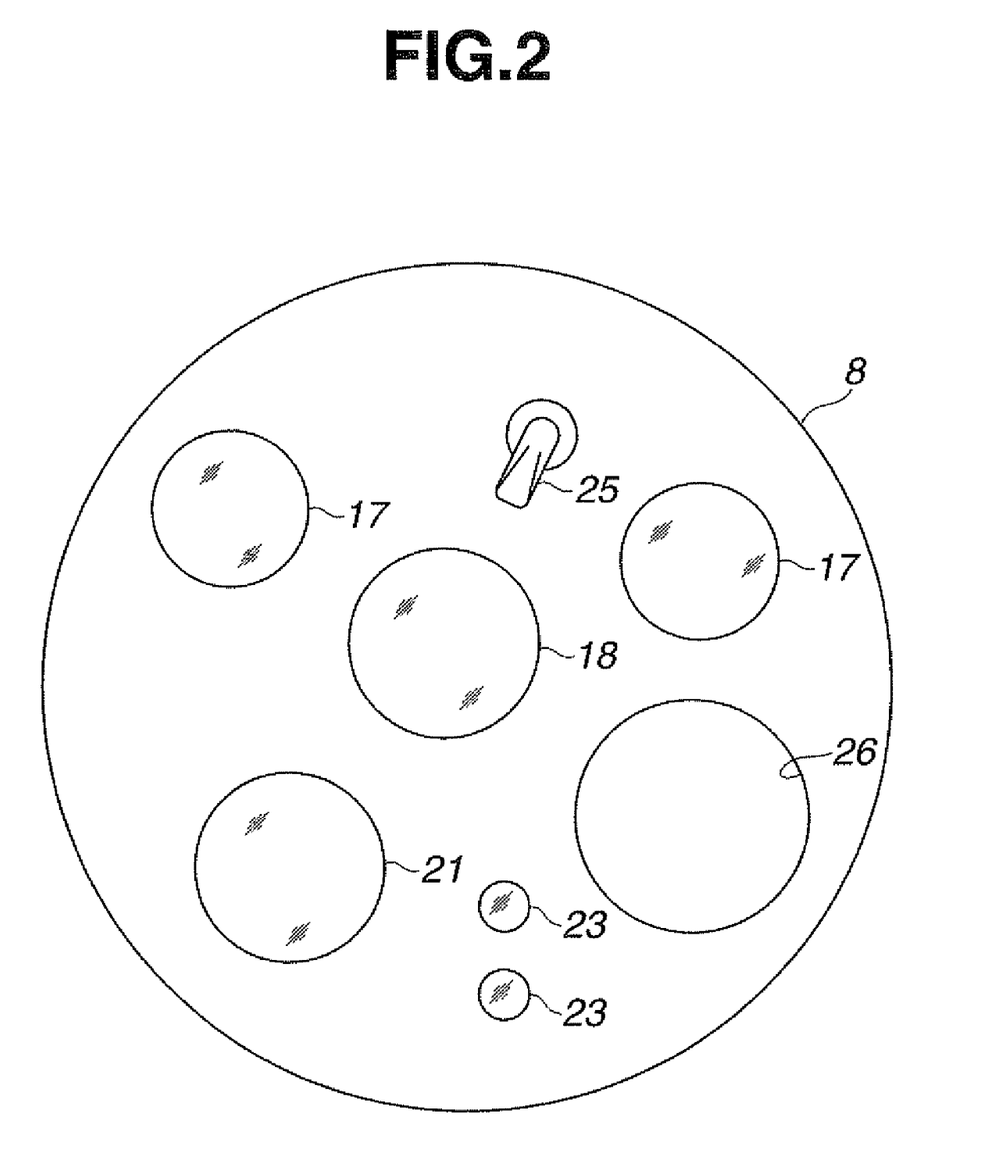
FIG. 2 relates to the first embodiment of the present invention and is a plan view showing a configuration of a distal end surface of an insertion portion of the endoscope apparatus.
Figure 3:
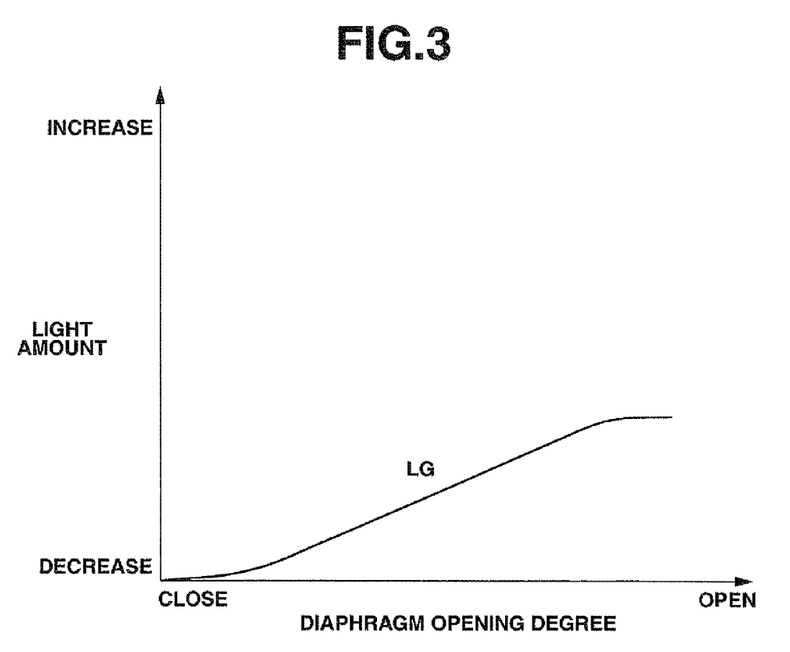
FIG. 3 relates to the first embodiment of the present invention and is a graph showing a relationship between opening degree of a diaphragm of a light source apparatus and the amount of a G reference light (excitation light) from a light guide fiber.
Figure 4:
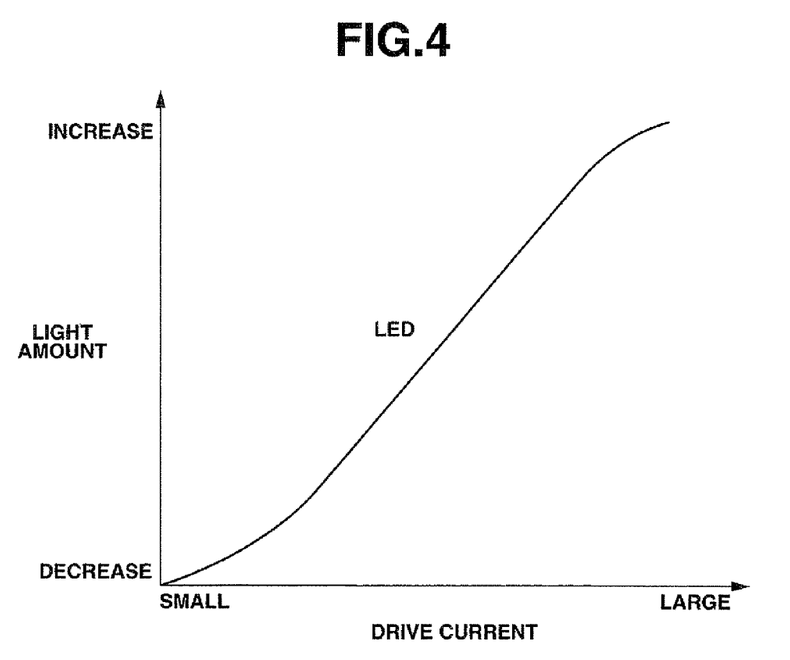
FIG. 4 relates to the first embodiment of the present invention and is a graph showing a relationship between supplied drive current and the amount of excitation light emitted by a light emitting diode.
Figure 5:
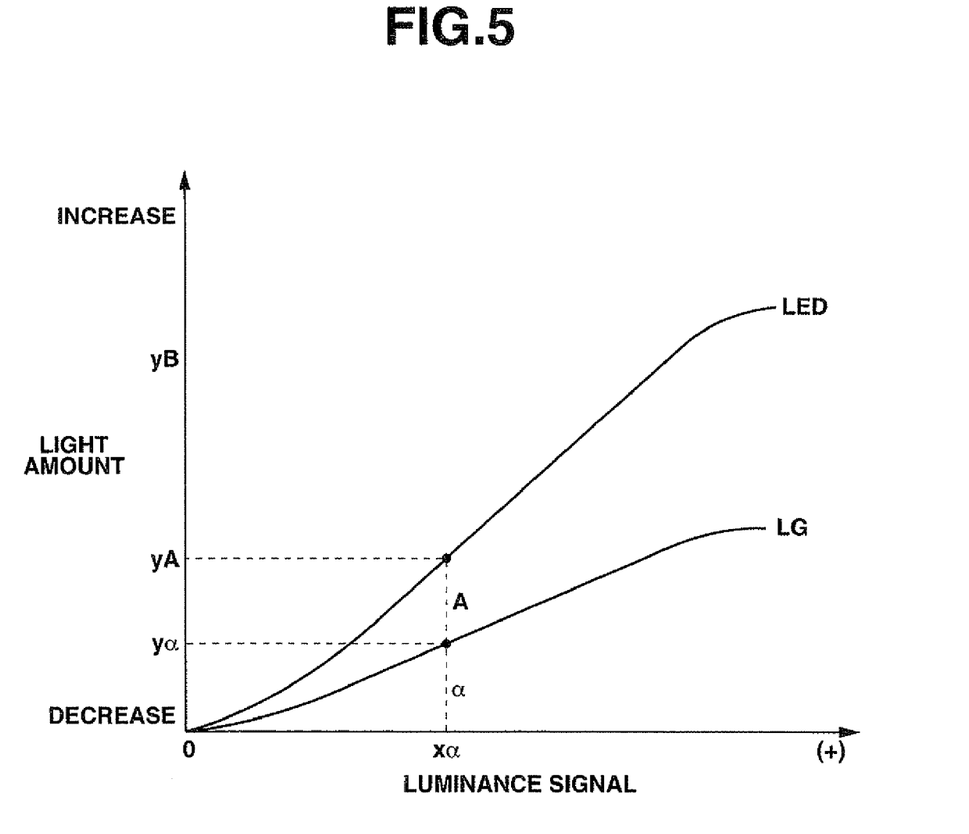
FIG. 5 relates to the first embodiment of the present invention and is a graph showing a state of change of a luminance signal of the excitation light and the light amount then at a constant ratio relative to the G reference light, in line with a set change amount of the drive current to be supplied to the light emitting diode for emitting the assisting excitation light, relative to the luminance signal of the G reference light and the light amount then of FIG. 3.

FIGS. 1 to 5 relate to a first embodiment of the present invention. FIG. 1 is a block diagram showing the entire configuration of an endoscope apparatus. FIG. 2 is a plan view showing a configuration of a distal end surface of an insertion portion of the endoscope apparatus. FIG. 3 is a graph showing a relationship between opening degree of a diaphragm of a light source apparatus and the amount of a G reference light from a light guide fiber. FIG. 4 is a graph showing a relationship between supplied drive current and the amount of excitation light emitted by a light emitting diode. FIG. 5 is a graph showing a state of change of a luminance signal of the excitation light and the light amount then at a constant ratio relative to the G reference light, in line with a set change amount of the drive current to be supplied to the light emitting diode for emitting the assisting excitation light, relative to the luminance signal of the G reference light and the light amount then of FIG. 3.

An endoscope apparatus 1 of the present embodiment shown in FIG. 1 has normal observation mode and fluorescent observation mode. The endoscope apparatus 1 mainly includes an electronic endoscope 2 to be inserted in a body cavity to observe the same; a light source apparatus 3 to generate an illumination light for normal observation and an excitation light for fluorescent observation; a processor 4 to perform signal processing to construct a normal observation image and a fluorescent image; and a monitor 5 to display an image obtained through normal light and an image obtained through fluorescent light.

The electronic endoscope (hereinafter simply referred to as "endoscope") 2 includes an elongate insertion portion 7 to be inserted into a body cavity. At a proximal portion of the endoscope 2 configuring an operation portion linked to the insertion portion 7 are disposed a change-over switch (SW) to switch between two image pickup means to be described below; a scope ID circuit 12 storing apparatus type information, etc.; and a scope switch (SW) 13 to perform instruction operations to select the normal observation mode or the fluorescent observation mode, and freeze and release instruction operations.

In the insertion portion 7 of the endoscope 2 is inserted a light guide fiber 9 to transmit the illumination light for normal observation or the excitation light for fluorescent observation. The light guide fiber 9 is inserted and provided up to a light source connector 1 provided at an incident end on a manual side. The light source connector 10 is detachably connected to the light source apparatus 3.

In the present embodiment, two electronic image pickup sections and two illumination portions are provided in a distal end portion 8 disposed at a distal end of the insertion portion 7.

One of the two electronic image pickup sections is a charge coupled device for normal observation (hereinafter described as "first CCD") 14, and the other is a charge coupled device for fluorescent observation (hereinafter described as "second CCD") 15. Note that the CCDs (Charge Coupled Devices) 14, 15 may employ a CMOS (Complementary Metal Oxide Semiconductor) image sensor, a CMD (Charged Modulation Device) image sensor, an AMI (Amplified MOS Imager), or a BCCD (Back Illuminated CCD) image sensor.

On respective front sides of the CCDs 14, 15 in the distal end portion 8, there are disposed in the following order from the side of the subject to be photographed: observation windows 18, 21 formed of a transparent member, of which surface is positioned to essentially agree with the distal end surface of the distal end portion 8; diaphragms 19 to spatially restrict an incident light amount for adjusting the focus from a distal point to a proximal point; and object lenses 20 as object optical systems for forming an optical image.

Note that only in immediate front of the second CCD 15, a barrier filter 22 is provided, which is an excitation light cut filter for cutting off excitation light. The barrier filter 22 is a filter for blocking emitted unnecessary excitation light so as to allow the second CCD 15 to accurately pick up autofluorescence of the biological tissues in fluorescent observation. For example, the barrier filter 22 has a characteristic to transmit a wavelength band of 460 to 700 nm, that is, a visible light excluding partial wavelengths (400 to 460 nm) of the blue band.

Furthermore, the second CCD 15 employs a highly precise imaging device that can obtain an image with higher image quality than the first CCD 14.

One of the two illumination portions is the light guide fiber 9 mentioned above for transmitting the illumination light or excitation light from the light source apparatus 3. The other is a blue light emitting diode (hereinafter denoted as "blue LED") 16, of which center wavelength is, e.g., 450 nm, for emitting an excitation light to assist the autofluorescence of the tissues to increase.

On the distal end surface of the distal end portion 8, two illumination windows 17, 23 formed by a transparent member are disposed to be respectively opposed to an end surface of the light guide fiber 9 and the LED 16 which are arranged in the distal end portion 8. Provided between the LED 16 and the illumination window 23 in the distal end portion 8 is an excitation light filter 24 that transmits only an excitation light of a predetermined wavelength region.

Note that as shown in FIG. 2, the distal end surface of the distal end portion 8 of the present embodiment is configured such that the observation window 18 corresponding to the first CCD 14 is arranged at the essential center, while on an outer circumferential side are arranged the observation window 21 corresponding to the second CCD 15, the two illumination windows 17, and the two illumination windows 23 corresponding to the LED 16. In other words, in the present embodiment the distal end portion 8 is provided with two LEDs 16, and excitation lights from the LEDs 16 are irradiated from the two illumination windows 23. On the distal end surface of the distal end portion 8 are disposed an air/water feeding nozzle 25 and a treatment instrument channel aperture 26 which are conventionally used.

Now returning to FIG. 1, a configuration of the light source apparatus 3 is described below.

The light source apparatus 3 of the present embodiment includes a lamp 32 that is driven to emit light by a lamp drive circuit 31 to radiate a light including from the infrared wavelength band to the visible light band; a change-over filter 38 provided in a light path of the lamp 32, of which rotational position is changed over by a motor 49; a light source diaphragm 35 that is provided in the illumination light path of the lamp 32, for restricting the light amount from the lamp 32; a change-over filter portion 30 provided in the illumination light path; and a condenser lens 41 for condensing light having passed through the change-over filter portion 30.

The change-over filter portion 30 is rotated by a rotating motor 39. The change-over filter portion 30 includes the change-over filter 38 having respective filters for normal and fluorescent observations to be arranged in the light path by a moving motor 37a. When the moving motor 37a rotationally drives a pinion 37 engaged with a rack 36 attached to the rotating motor 39, the change-over filter 38 is slidingly moved with the rotating motor 39 in a direction perpendicular to the optical axis.

Though not shown, the change-over filter 38 includes RGB filters for normal illumination on an inner circumferential side and filters for fluorescent illumination on an outer circumferential side, which are concentrically provided. In other words, in the present embodiment, driving the moving motor 37a can change over between the action state in a normal image mode (also referred to as "normal mode") where the filter for normal illumination is set in the light path, and the action state in a fluorescent image mode (also referred to as "fluorescent mode") where the filter for normal illumination is changed over to the filters for fluorescent illumination to be set.

Note that the RGB filters for normal illumination include an R filter, G filter and B filter for respectively transmitting lights of R (red), G (green) and B (blue) wavelength bands, that are provided trisected in a circumferential direction. The RGB filters are rotationally driven by the rotating motor 39 to be sequentially and essentially continually positioned in the light path.

Transmission characteristics of the R, G, B filters for normal illumination are set such that the R filter transmits light of a wavelength range of 600 to 700 nm, the G filter of 500 to 600 nm, and the B filter of 400 to 500 nm, for example.

On the other hand, the filters for fluorescent illumination include R, G and B filters to respectively transmit narrow-band Red (R), narrow-band Green (G), and narrow band excitation light (B) which are provided trisected in the circumferential direction, on an outer circumferential side of the change-over filter 38 than the filters for normal observation. The filters for fluorescent illumination are rotationally driven by the rotating motor 39 to be sequentially positioned in the light path.

Transmission characteristics of the filters for fluorescent illumination are set such that the R filter transmits light of a wavelength range of 640 to 660 nm, the G filter of 540 to 560 nm, and the B filter of 400 to 440 nm, for example.

In addition, a change-over filter 33 arranged just before the lamp 32 is configured such that a plurality of filters are rotated by a rotating motor 34 to be each positioned in the illumination light path. The change-over filter 33 includes a filter that transmits the visible light substantially without restriction, as well as at least one filter to restrict the wavelength of the excitation light to be irradiated to the subject side depending on the endoscope 2 connected for use in the fluorescent mode. Note that the change-over filter 33 may in some cases include a filter to impose restriction in wavelength range on an infrared illumination light for infrared observation.

The illumination light from the light source apparatus 3 is thus transmitted to the distal end side of the insertion portion 7 of the electronic endoscope 2 through the light guide fiber 9 mentioned above. The light guide fiber 9 transmits the light for fluorescent observation and the light for normal observation with small transmission loss. Note that the light guide fiber 9 is configured of, e.g., multicomponent-system glass fiber, quarts fiber, etc.

The light transmitted to the distal end surface of the light guide fiber 9 passes through the illumination window 17 mounted at a position opposed to the distal end surface, to be expanded and irradiated onto the observation target region side in the body cavity.

Next, a configuration of the processor 4 is described below.

The processor 4 of the present embodiment includes a control unit 50, a light adjustment circuit 51 configuring a light adjustment section provided in the control unit 50, an apparatus type detection circuit 52, a CCD drive circuit 53, an LED drive circuit 54, a preamplifier 55, an automatic gain control (AGC) circuit 56, an A/D conversion circuit 57, a multiplexer 58, three frame memories 61 to 63, an image processing circuit 64 as an image creation section, and a D/A conversion circuit 65.

In the processor 4, an image signal from the CCDs 14, 15 inputted through the switching SW of the endoscope 2 is amplified by the preamplifier 55, further amplified by the AGC circuit 56 to a predetermined level, to be then converted by the A/D conversion circuit 57 from an analog signal to a digital signal (image data).

Each of the image data is passed through the multiplexer 58 that performs change-over operation and temporarily stored (memorized) in the first frame memory 61, the second frame memory 62, and the third frame memory 63.

The image data stored in the frame memories 61 to 63 are inputted in the image processing circuit 64 to be subjected to outline emphasis, etc., thereafter converted into analog RGB signals by the D/A conversion circuit 65 and outputted to the monitor 5.

The light adjustment circuit 51 of the processor 4 automatically controls the opening amount of the light source diaphragm 35 in the light source apparatus 3, based on a signal through the preamplifier 55. The light adjustment circuit 40 is controlled by the control unit 50.

The control unit 50 controls a lamp current for light-emission drive of the lamp 32 by the lamp drive circuit 31 of the light source apparatus 3. The control unit 50 performs control actions for various endoscope functions in response to an operation of the scope SW 13 of the endoscope 2.

Note that the CCD drive circuit 53 is controlled by the control unit 50. Specifically, in the normal mode, the CCD drive circuit 53 drives the first CCD 14 switched for drive by a change-over switch (SW) 11 and activates an electronic shutter function to optimize the amount of light to be received by the first CCD 14.

Also in the fluorescent mode, the CCD drive circuit 53 drives the second CCD 15 switched for drive by the change-over SW 11 and activates the electronic shutter function to optimize the amount of autofluorescence of the subject to be received by the second CCD 15.

Moreover, the control unit 50 controls the moving motor 37*a* of the light source apparatus 3 based on a selected mode. The rotating motor 39 of the light source apparatus 3 is controlled by the control unit 50. An output of an encoder, not shown, mounted to the rotation shaft of the rotating motor 39, etc. is inputted to the control unit 50.

Then, in synchronization with the output of the encoder, the control unit 50 controls the CCD drive circuit 53, change-over of the multiplexer 58, and the like. In controlling change-over of the multiplexer 58, the control unit 50 in the normal mode controls to sequentially store image data picked up under the illumination through the R, G, B filters for normal observation respectively into the first frame memory 61, the second frame memory 62, and the third frame memory 63.

On the other hand, also in the fluorescent mode, the control unit 50 controls change-over of the multiplexer 58 to sequentially store image data picked up under the illumination through the R, G, B filters for fluorescent observation respectively into the first frame memory 61, the second frame memory 62, and the third frame memory 63.

Note that the control unit 50 is configured to switch and use the plurality of filters provided to the change-over filter 33, i.e., a filter not restricting the band, and at least one filter (two in the present embodiment) restricting the band, depending on the apparatus type information of the connected endoscope detected by the apparatus type detection circuit 52 from the scope ID circuit 12 of the endoscope 2, or depending on the observation situation.

When the scope SW 13 of the endoscope 2 is operated to make, e.g., an instruction for the fluorescent image mode or the normal image mode, the operation signal is inputted to the control unit 50. The control unit 50 then performs a control action corresponding to the operation signal.

For example, when a normal mode switch of a mode change-over switch of the scope SW 13 is operated, the light source apparatus 3 sequentially supplies the light guide fiber 9 with the illumination lights of the normal mode, that is, R, G, B lights for normal illumination. The processor 4 performs an image signal processing corresponding to the normal mode on an image signal photoelectrically converted by the first CCD 14.

On the other hand, when a fluorescent mode switch of the mode change-over switch is operated, the light source apparatus 3 sequentially supplies the light guide fiber 9 with the illumination lights of the fluorescent mode, that is, R, G, B lights for fluorescent illumination. At this moment, the light adjustment circuit 51 of the control unit 50 of the processor 4 outputs a brightness signal to the image processing circuit 64, and drives the LED drive circuit 54 in synchronization with the open/close state of the light source diaphragm 35 of the light source apparatus 3. The LED drive circuit 54 is then controlled by the light adjustment circuit 51 to supply the LED 16 of the endoscope 2 with a controlled drive current having a predetermined pulse width.

This causes the LED 16 to irradiate a blue light to serve as the excitation light at a light amount adjusted to the drive current value from the illumination window 23 to the tissues to be examined via the excitation light filter 24.

At this time, the processor 4 performs an image signal processing corresponding to the fluorescent mode, on an image signal photoelectrically converted by the second CCD 15. In addition, the image processing circuit 64 combines an autofluorescence image signal and a G reflection image signal and outputs to the monitor 5 an image signal to provide a pseudo color display of the change in intensity of the autofluorescence as change in color tone.

Note that the two CCDs 14, 15 for normal observation and fluorescent observation, respectively, are switched for drive by the change-over SW 11, to be driven by a CCD drive signal from the CCD) drive circuit 53 provided in the processor 4. An optical image formed on each of the CCDs 14, 15 in drive state is photoelectrically converted into an image signal, which is transmitted to the change-over SW 11.

Here, e.g., the processor 4 if with a conventional configuration would in the fluorescent observation mode have the image processing circuit 64 assign the autofluorescence image to green, and the G reflection image to red and blue, to provide a pseudo color display on the monitor 5. In other words, AFI (Autofluorescence Imaging) white balance is performed, in which, to allow normal tissues to have a bright green color, the amplification ratio of the autofluorescence is changed in the processor 4 to make the autofluorescence intensity on par with that of the G reflection light. As a result, a neoplastic lesion such as cancer is attenuated in autofluorescence intensity into a magenta color tone. At this time, in an endoscope apparatus having the conventional configuration, the weak autofluorescence intensity is amplified by the processor 4, unavoidably resulting in a noisy fluorescent observation image to be displayed on the monitor 5.

To overcome this problem, the endoscope apparatus 1 of the present embodiment performs a light adjustment control to increase/decrease the light amount of the excitation light assisted by the LED 16 in line with the increase/decrease of the amount of the illumination light transmitted by the light guide fiber 9 from the light source apparatus 3, while maintaining the color balance (amplification ratio of the autofluorescence and G reflection light) performed by the processor 4, at a predetermined, i.e., constant level. Note that, in the fluorescent observation mode, R reference light may be used.

Here, using FIGS. 3 to 5, there is elaborated an example of drive control of the light source apparatus 3 and the LED 16 performed by the control unit 50 of the processor 4 in the fluorescent observation mode for the tissues to be examined by the endoscope apparatus 1 of the present embodiment configured as described above.

First, as shown in FIG. 3, the illumination light of the G reference light (excitation light) transmitted from the light source apparatus 3 and irradiated from the light guide fiber 9 (designated as "LG" in the drawing) is changed or increased/decreased in amount according to the opening degree or open/close state of the diaphragm. The amount of the illumination light of the light guide fiber 9 is increased/decreased to change according to the distance from each image forming position of the CCDs 15, 16 to the tissues to be examined.

In the present embodiment, the image obtained by each of the CCDs 14, 15 is used by the control unit 50 to perform white balance according to which the light adjustment circuit 51 controls to open/close the light source diaphragm 35 of the light source apparatus 3.

On the other hand, as shown in FIG. 4, there is also set excitation light for assistance for a predetermined light amount that allows obtaining a good autofluorescence image of the tissues to be examined even if the color balance (amplification ratio of the autofluorescence and the G reflection light) is held at a predetermined (constant) level in the fluorescent observation mode. That is, in line with the graph of FIG. 4 and in synchronization with the open/close state of the light source diaphragm 35 of the light source apparatus 3 by the light adjustment circuit 51, the drive current supplied to the LED 16 from the light adjustment circuit 51 of the control unit 50 is changed, and in line therewith the increase/decrease of the excitation light emission amount is controlled.

Specifically, the control unit 50 controls driving of the light adjustment circuit 51 according to the luminance signal representing the brightness of the tissues to be examined (subject) to be photographed such that the ratio between the amount of the G reference light (excitation light) irradiated from the light guide fiber 9 and the light amount of the LED 16 is constant, as shown in FIG. 5. Note that this luminance signal represents the brightness of the screen that configures an image that is photographed by the second CCD 15 with an amount of illumination light from the light source apparatus 3 increased/decreased by the open/close state of the light source diaphragm 35 and rendered into image data.

To elaborate, in the drawing, let a light amount yα of the G reference light from the light guide fiber 9 for an arbitrary luminance signal xα be α, and let a difference (yA−yα) between a light amount yA of the LED 16 and the light amount y α for the arbitrary luminance signal xα be A. That is, the light adjustment circuit 51 of the control unit 50 changes the drive current of the LED 16 in synchronization with the open/close state of the light source diaphragm 35 of the light source apparatus 3 such that the ratio between α and A (α:A) becomes constant. In other words, the light adjustment circuit 51 of the control unit 50 changes the opening degree of the light source diaphragm 35 and the drive current of the LED 16 in line with the change of the luminance signal such that the ratio between the amount of the G reference light irradiated from the light guide fiber 9 and the light amount of the LED 16 becomes constant. Note that the changing of the light amount of LED 16 may be controlled by changing the pulse width of the drive current that the light adjustment circuit 51 of the control unit 50 supplies to the LED 16.

As appreciated from the above, the endoscope apparatus 1 of the present embodiment, which is configured to increase the autofluorescence intensity by the assistant excitation light of the LED 16, can perform light adjustment maintaining the color balance (amplification ratio between the autofluorescence and G reflection light) at a predetermined (constant) level. In other words, the autofluorescence intensity is not amplified by the image processing circuit 64, which eliminates the amplification noise from the fluorescent observation image displayed on the monitor 5, allowing for a clear fluorescent observation image.

Second Embodiment

Next, a second embodiment is described. Note that in the present embodiment, components described with the endoscope apparatus of the first embodiment use the same symbols, omitting detailed descriptions thereof.

Figure 6:
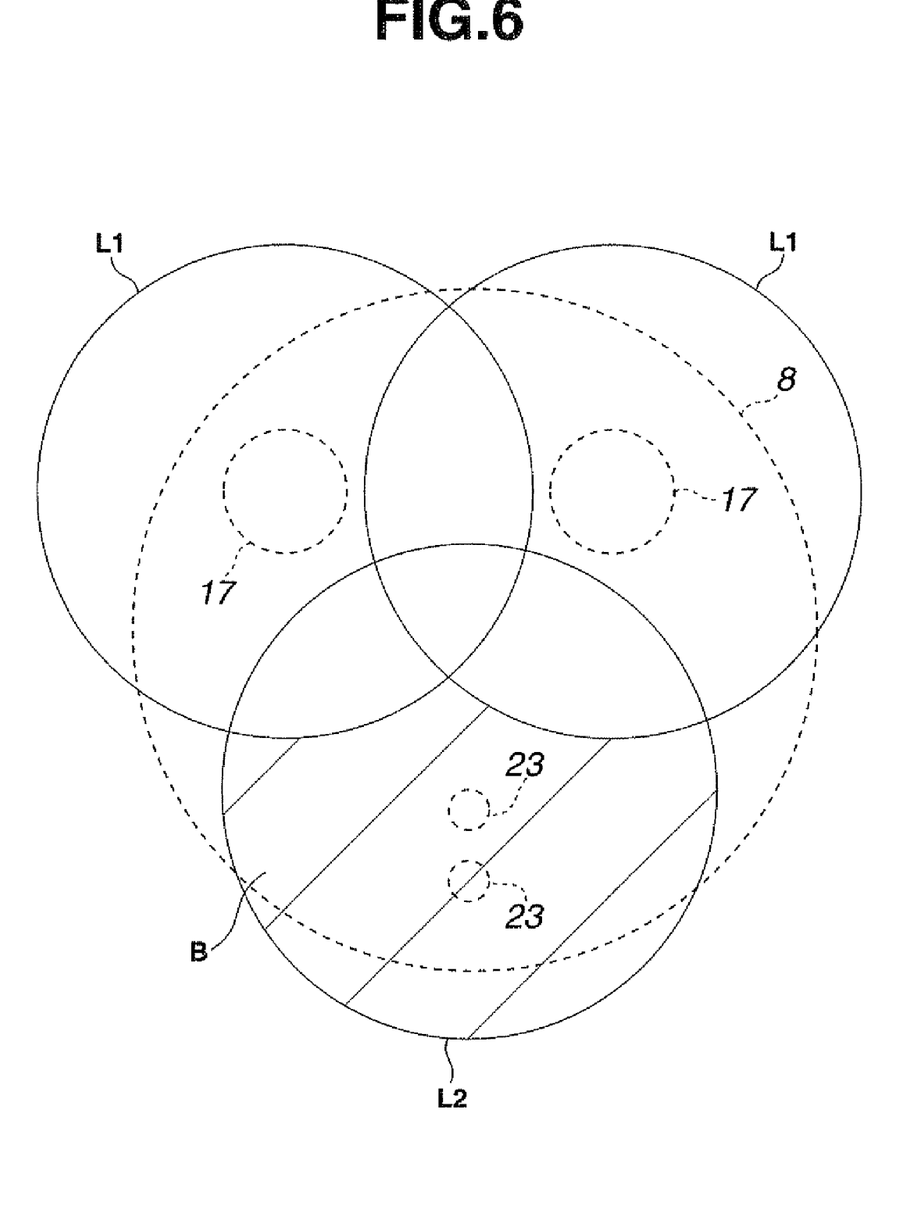
FIG. 6 relates to a second embodiment of the present invention and is a view showing a distribution state of the illumination light (G reference light) and the assistant excitation light irradiated from the distal end surface of the insertion portion to close-by tissues to be examined in a fluorescent observation mode.
Figure 7:
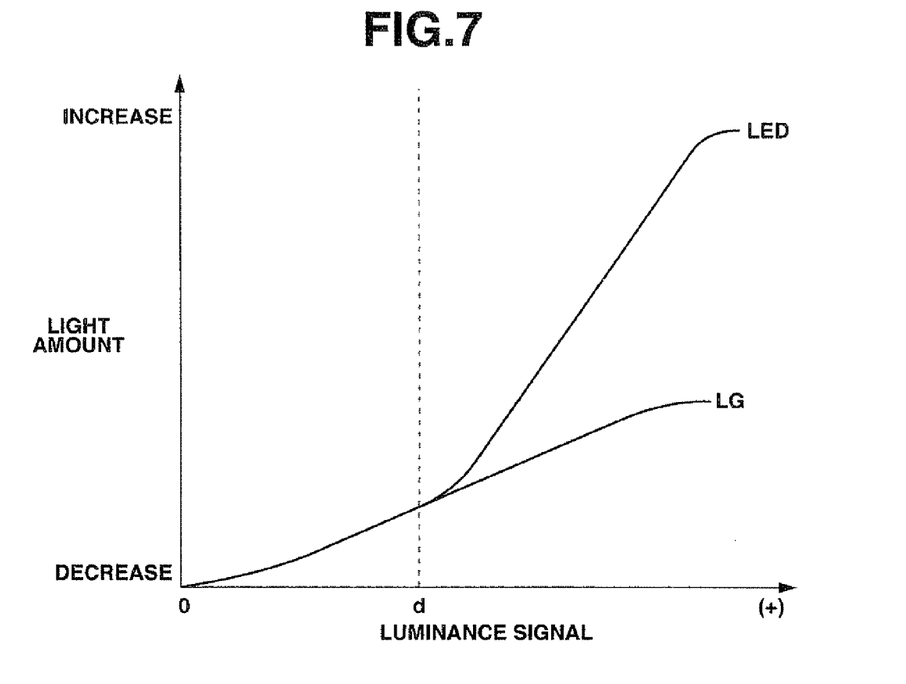
FIG. 7 relates to the second embodiment of the present invention and is a graph showing a state of change of a luminance signal of the excitation light by the light emitting diode and the light amount then, relative to the luminance signal of the G reference light and the light amount then.
Figure 8:
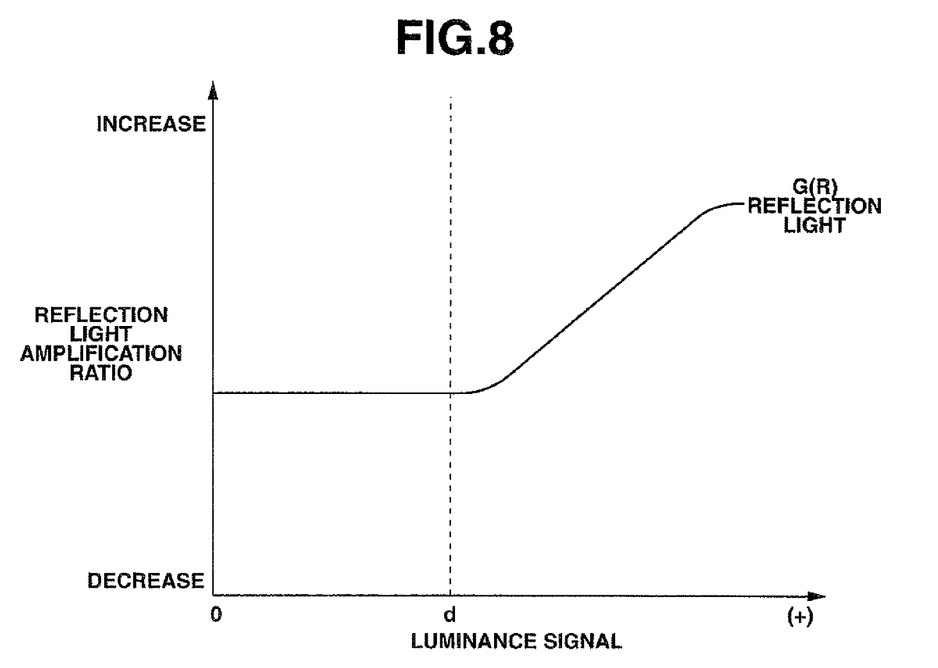
FIG. 8 relates to the second embodiment of the present invention and is a graph showing a change of amplification ratio of a G (R) reflection light with respect to the luminance signal corresponding to that of FIG. 7.

FIGS. 6 to 8 relate to a second embodiment of the present invention. FIG. 6 is a view showing a distribution state of the illumination light (G reference light) and the assistant excitation light irradiated from the distal end surface of the insertion portion to close-by tissues to be examined in a fluorescent observation mode. FIG. 7 is a graph showing a state of change of a luminance signal of the excitation light by the light emitting diode and the light amount then, relative to the luminance signal of the G reference light and the light amount then. FIG. 8 is a graph showing a change of amplification ratio of a G (R) reflection light with respect to the luminance signal of FIG. 7.

In the fluorescent observation mode, in a state where, e.g., the distance between the distal end portion 8 of the endoscope 2 shown in broken line and the tissues to be examined is close, unevenness occurs in a light distribution range L1 of the illumination light transmitted through the light guide fiber 9 from the light source apparatus 3 and irradiated from the two illumination windows 17, and in a light distribution range L2 of the assistant excitation light irradiated from the two illumination windows 23 by the LED 16, as shown in FIG. 6.

That is, when the distance to the tissues to be examined is that of proximal observation, the overlapping part between the light distribution range L1 of the (R) GB illumination light including the G reference light (excitation light) from the light source apparatus 3 and the light distribution range L2 of the excitation light from the LED 16 is small. This results in creation of an irradiation range B shown in broken line of only the excitation light from the LED 16.

Consequently, the illumination light from the light source apparatus 3 and the excitation light from the LED 16 has uneven coloring where only the irradiation range B is blue. This further causes uneven coloring in the autofluorescence of the tissues to be examined.

To eliminate this problem, the endoscope apparatus 1 of the present embodiment causes the control unit 50 to control the light source diaphragm 35 of the light source apparatus 3 and the drive current of the LED 16, or pulse width of this drive current, thereby controlling the light amount according to the luminance signal as shown in FIG. 7. In synchronization with this light amount control, the control unit 50 also controls the amplification ratio of the G (R) reflection light according to the luminance signal, as shown in FIG. 8.

Specifically, let the value of a given luminance signal be a threshold value d, as shown in FIGS. 7, 8. The threshold value d is set to a value of the luminance signal at a position near a border of whether or not an uneven light distribution as mentioned above occurs and where no uneven coloring occurs in the photographed fluorescent observation image, in the separation distance from the tissues to be examined to the distal end surface of the distal end portion 8 of the endoscope 2. Note that the separation distance mentioned here is precisely the distance from the illumination window 17 to the subject.

In other words, when the luminance signal has a value smaller than the threshold value d as shown in FIG. 7, the endoscope apparatus 1 of the present embodiment performs control to a state where the drive current to the LED 16 is stopped or the LED 16 is supplied with a drive current to cause a feeble light emission, so as to avoid an occurrence of uneven light distribution in the illumination light from the light source apparatus 3 and the excitation light from the LED 16.

To elaborate further, when the luminance signal is smaller than the threshold value d, the control unit 50 of the endoscope apparatus 1 stops the drive signal from the light adjustment circuit 51 to the LED drive circuit 54 or outputs a feeble current supply to turn off the LED 16 or make the LED 16 emit a feeble light.

In this state, where the separation distance from the tissues to be examined to the distal end surface of the distal end portion 8 of the endoscope 2 is proximal, the illumination light from the light source apparatus 3 alone allows for a sufficient autofluorescence of the tissues to be examined, thus preventing uneven light distribution by the light emission of the LED 16.

Then, when the luminance signal reaches the threshold value d, the control unit 50 of the endoscope apparatus 1 outputs a drive signal from the light adjustment circuit 51 to the LED drive circuit 54 to have the LED 16 emit light for assistant irradiation of the excitation light on the tissues to be examined.

That is, when the fluorescent observation region is at a distance not less than the predetermined distance that prevents the occurrence of uneven light distribution in the separation distance from the tissues to be examined to the distal end surface of the distal end portion 8 of the endoscope 2, that is, when the luminance signal is not less than the threshold value d, the control unit 50 controls by the light adjustment circuit 51 the illumination light from the light source apparatus 3 as well as the excitation light from the LED 16 in a synchronous manner as shown in the graph of FIG. 7.

In the fluorescent observation region, where the light emission of the LED 16 has started assisting the excitation light, there is a loss of color balance between the autofluorescence of the tissues to be examined and the G (R) reflection light by the illumination light from the light source apparatus 3. Accordingly, the amplification ratio of the G (R) reflection light is changed according to the value of the luminance signal (separation distance from the tissues to be examined to the distal end surface of the distal end portion 8 of the endoscope 2) as shown in FIG. 8. In other words, here, the image processing circuit 64 changes the amplification ratio of the G (R) reflection light in line with the light amount of the LED 16, because if the assistant excitation light is emitted from the LED 16 with the amplification ratio of the autofluorescence and the G (R) reflection light maintained constant, loss of color balance occurs.

In other words, the image data of the G (R) reflection light is amplified synchronously according to the change of the light amount of the light emission by the LED 16 so as to maintain the state of color balance when the LED 16 is not emitting light. Note that image data of the autofluorescence may be amplified with such an amplification rate as to minimize noise generation as much as possible.

As appreciated from the foregoing, the endoscope apparatus 1 of the present embodiment controls the assistant excitation light by the LED 16 so as to avoid the uneven coloring that occurs when the separation distance from the tissues to be examined to the distal end surface of the distal end portion 8 of the endoscope 2 is proximal, while when the separation distance from the tissues to be examined to the distal end surface of the distal end portion 8 of the endoscope 2 is distal, the endoscope apparatus 1 amplifies the image data of the G (R) reflection light. The endoscope apparatus 1 can thus display a good fluorescent observation screen with a good color balance on the monitor 5.

Third Embodiment

Next, a third embodiment is described. Note that also in the present embodiment, components described with the endoscope apparatus of the first and the second embodiments use the same symbols, omitting detailed descriptions thereof.

Figure 9:
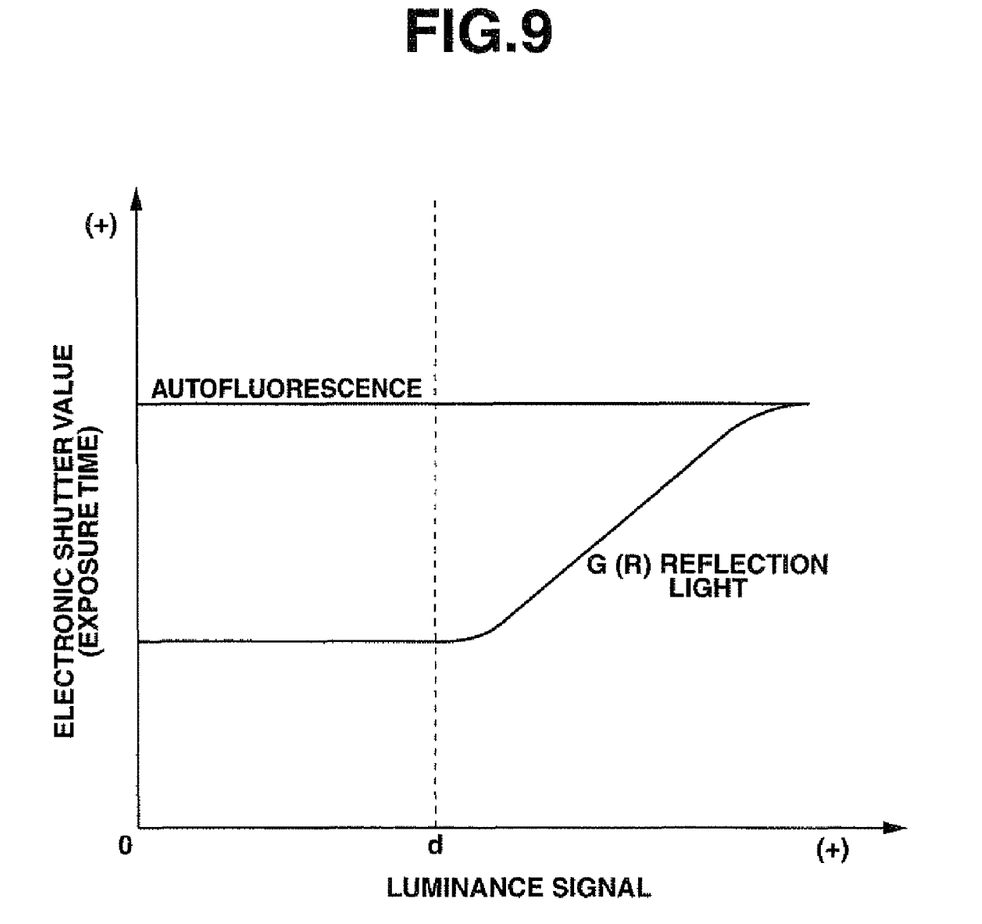
FIG. 9 relates to a third embodiment of the present invention and is a graph showing a change of electronic shutter value (exposure time) of the G (R) reflection light with a constant electronic shutter value (exposure time) of autofluorescence, relative to the luminance signal corresponding to that of FIG. 7.
Figure 10:
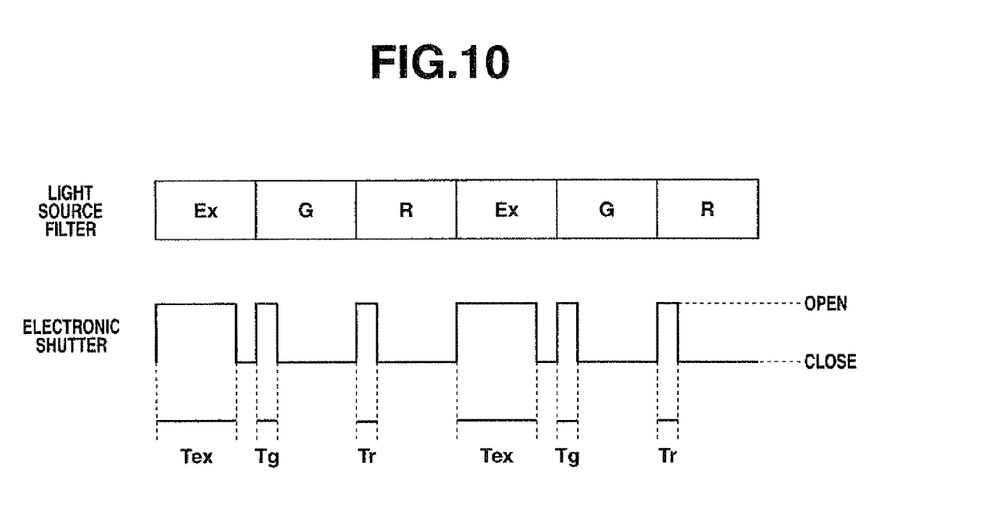
FIG. 10 relates to the third embodiment of the present invention and is a view showing electronic shutter values (CCD exposure times) of the autofluorescence, the G reflection light, and the R reflection light when the light emitting diode is turned off.
Figure 11:
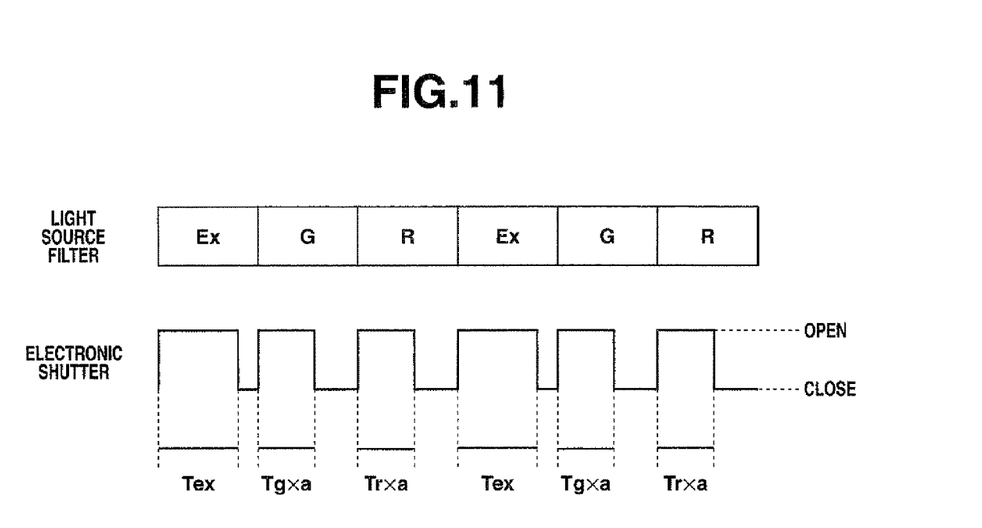

FIGS. 9 to 11 relate to the third embodiment of the present invention. FIG. 9 is a graph showing a change of an electronic shutter value (exposure time) of the G (R) reflection light with a constant electronic shutter value (exposure time) of autofluorescence, relative to the luminance signal corresponding to that of FIG. 7. FIG. 10 is a view showing electronic shutter values (CCD exposure times) of the autofluorescence, the G reflection light, and the R reflection light when the light emitting diode is turned off. FIG. 11 is a view showing electronic shutter values (CCD exposure times) of the autofluorescence, the G reflection light, and the R reflection light when the light emitting diode is turned on.

The present embodiment shows the endoscope apparatus 1 configured to allow displaying a good fluorescent observation screen with a good color balance on the monitor 5 without causing uneven coloring in the autofluorescence of the tissues to be examined as well as without amplifying the image data, as in the second embodiment.

Like the second embodiment, the endoscope apparatus 1 of the present embodiment has the control unit 50 control the light source diaphragm 35 of the light source apparatus 3 and the drive current of the LED 16 to control the amount of the illumination light and excitation light according to the luminance signal as shown in FIG. 7.

At this time, the second embodiment changed the amplification ratio of the G (R) reflection light according to the value of the luminance signal for the fluorescent observation region where light emission of the LED 16 has started assisting the excitation light.

In contrast, the endoscope apparatus 1 of the present embodiment uses an electronic shutter function that sets an exposure time by sweeping out an electric charge accumulated in the second CCD 15 to a base, thereby controlling to change the electronic shutter value of the G (R) reflection light (exposure time) leaving the electronic shutter value (exposure time) of the autofluorescence constant or unchanged, according to the separation distance (luminance signal) from the tissues to be examined to the distal end surface of the distal end portion 8 of the endoscope 2, as shown in FIG. 9.

This control of the electronic shutter value is performed by the light adjustment circuit 51 of the control device 50 controls through the CCD drive circuit 53.

In other words, in a region where the separation distance from the tissues to be examined to the distal end surface of the distal end portion 8 of the endoscope 2 is distal, in which the luminance signal is not less than the threshold value d and the assistant excitation light emitted by the LED 16, the electronic shutter value is changed so as to increase the exposure time of the G (R) reflection light in synchronization with the increase of the amount of excitation light by the light emission of the LED 16.

Specifically, in a region where the separation distance from the tissues to be examined to the distal end surface of the distal end portion 8 of the endoscope 2 is proximal, in which turning on the LED 16 results in uneven light distribution, e.g. exposure time of autofluorescence is taken as time period Tex, and exposure time of G (R) reflection light as time period Tg (Tr), as shown in FIG. 10.

On the other hand, in a region where the separation distance from the tissues to be examined to the distal end surface of the distal end portion 8 of the endoscope 2 is distal, the exposure time of the G (R) reflection light is changed, in line with the trajectory of the graph of FIG. 9, to time period Tg×a (Tr×a), where time period Tg is multiplied by a predetermined variable magnification a which is in accordance with the increase/decrease of the luminance signal, while maintaining the exposure time of autofluorescence at time period Tex, as shown in FIG. 11.

In other words, as in the second embodiment, the endoscope apparatus 1 of the present embodiment controls the assistant excitation light by the LED 16 so as to avoid the uneven coloring that occurs when the separation distance from the tissues to be examined to the distal end surface of the distal end portion 8 of the endoscope 2 is proximal, while in a region where the separation distance from the tissues to be examined to the distal end surface of the distal end portion 8 of the endoscope 2 is distal, the endoscope apparatus 1 controls the exposure time of the G (R) reflection light of the second CCD 15, to allow reducing the noise occurrence due to amplification of the image data of the G (R) reflection light. The endoscope apparatus 1 can thereby display a good fluorescent observation image with a good color balance on the monitor 5.

Note that in the present embodiment, the separation distance from the tissues to be examined to the distal end surface of the distal end portion 8 of the endoscope 2 may be measured by a distance detection unit in the control unit 50 that detects the distance through approximate calculation based on the open/close state of the light source diaphragm 35, or a distance detection unit that configures a brightness detection unit that detects a luminance signal by an image brightness, as well as, e.g., an optical sensor that configures a distance detection unit. Furthermore, the endoscope 2 of the present embodiment, which includes two image pickup means which are CCDs, may of course be configured to pick up images in normal observation and fluorescent observation with one image pickup means.

The inventions described in the above-mentioned embodiments are not limited to the embodiment and modification examples thereof, but various other kinds of modifications can be implemented without departing from the scope the invention in the practical phase. Moreover, the above embodiments include inventions at various stages and appropriate combinations of the disclosed multiple constituent features can extract various inventions.

For example, if a problem to be solved by the invention can be solved and the described effects be attained despite deletion of some of the entire constituent features shown in the embodiment, then the configuration without the some deleted constituent features can be extracted as an invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

The invention claimed is:

1. A medical apparatus comprising:
   a first illumination window through which a first illumination light from a first light source is irradiated to a subject;

a second illumination window provided at a position different from that of the first illumination window, through which a second illumination light from a second light source is irradiated to the subject;

an electronic image pickup section which picks up an image of the subject;

an image creation section which generates an observation image based on an image pickup signal obtained by the electronic image pickup section;

a light adjustment section which synchronously adjusts respective amounts of illumination lights irradiated from the first illumination window and the second illumination window;

a control unit which controls the light adjustment section or the image creation section such that a color tone of the observation image is maintained to a predetermined color tone according to an increase or decrease of the amount of the illumination light from the first illumination window; and a distance detection unit which detects a distance between the first illumination window and the subject, wherein the control unit controls, through the light adjustment section, to change over between a state where the second light source is turned off and a state where the second light source emits a light in line with an amount of light irradiated from the first illumination window, depending on a detection result by the distance detection unit.

2. The medical apparatus according to claim 1, wherein the control unit controls the light adjustment section or the image creation section such that a ratio of the light amounts of the first illumination light and the second illumination light becomes constant.

3. The medical apparatus according to claim 2, wherein
the first light source is a light source lamp of a light source apparatus, which irradiates the first illumination light, from a light guide fiber for introducing a light from the source lamp for irradiation, from the first illumination window to the subject;
the second light source is an LED, which irradiates a light from the LED to the subject from the second illumination window, and
the light adjustment section synchronously adjusts each of the illumination lights by opening/closing a diaphragm which shields and adjusts the light of the source lamp to a predetermined light amount and increasing/decreasing a drive current to be supplied to the LED) or changing a pulse width of the drive current.

4. The medical apparatus according to claim 3, further comprising an endoscope which includes an insertion portion having a distal end provided with an irradiating end portion of the light guide fiber, the LED, and the electronic image pickup section.

5. The medical apparatus according to claim 1, wherein the control unit controls the image creation section to generate the observation image by changing an amplification ratio of an image-pickup signal in a manner corresponding to a light of a predetermined wavelength according to respective changed amounts of the adjusted illumination lights.

6. The medical apparatus according to claim 1, wherein the distance detection unit detects a distance between the first illumination window and the subject based on a luminance signal configuring brightness of the observation image.

7. The medical apparatus according to claim 1, wherein:
the first light source is a light source lamp of a light source apparatus, which irradiates the first illumination light, from a light guide fiber for introducing light from the source lamp for irradiation, from the first illumination window to the subject;
the medical apparatus includes a diaphragm which is controlled to open/close by the light adjustment section to shield and adjust the light of the source lamp to a predetermined amount of light; and
the distance detection unit approximately calculates a distance between the first illumination window and the subject based on an opening/closing amount of the diaphragm.

8. The medical apparatus according to claim 7, wherein the control unit changes an amplification ratio of an image-pickup signal that corresponds to a light of a predetermined wavelength, in a state where the second light source is emitting light.

9. The medical apparatus according to claim 8, wherein
the second light source is an LED, and
the light adjustment section adjusts an amount of light of the second illumination by changing a drive current to be supplied to the LED or a pulse width of the drive current.

10. The medical apparatus according to claim 9, further comprising an endoscope which includes an insertion portion having a distal end provided with an irradiating end portion of the light guide fiber, the LED, and the electronic image pickup section.

11. The medical apparatus according to claim 7, wherein
the electronic image pickup section includes an exposure time adjustment section which adjusts exposure time, and
the exposure time adjustment section changes exposure time of the electronic image pickup section with respect to a light of a specific wavelength in a state where the second light source is emitting light.

12. The medical apparatus according to claim 11, further comprising an endoscope which includes an insertion portion having a distal end provided with an irradiating end portion of the light guide fiber, the LED, and the electronic image pickup section.

* * * * *